United States Patent
Morales et al.

(10) Patent No.: US 8,048,077 B2
(45) Date of Patent: Nov. 1, 2011

(54) STERNUM CLOSURE DEVICE

(75) Inventors: Pedro Morales, Tuttlingen (DE); Dieter Weisshaupt, Immendingen (DE); Theodor Lutze, Balgheim (DE); Manfred Dworschak, Duerbheim (DE); Leon Eijsman, Blaricum (NL)

(73) Assignee: Aesculap AG, Tuttlingen (DE)

( * ) Notice: Subject to any disclaimer, the term of this patent is extended or adjusted under 35 U.S.C. 154(b) by 167 days.

(21) Appl. No.: 12/380,977

(22) Filed: Mar. 4, 2009

(65) Prior Publication Data

US 2009/0234357 A1   Sep. 17, 2009

Related U.S. Application Data

(63) Continuation of application No. PCT/EP2007/006846, filed on Aug. 2, 2007.

(30) Foreign Application Priority Data

Sep. 22, 2006 (DE) .......................... 10 2006 046 428

(51) Int. Cl.
*A61B 17/56* (2006.01)

(52) U.S. Cl. .............................. 606/71; 606/70; 606/280

(58) Field of Classification Search .................... 16/225, 16/251; 24/168–177, 485, 531; 606/70–71, 606/279–299, 902–906
See application file for complete search history.

(56) References Cited

U.S. PATENT DOCUMENTS

| 3,693,616 | A | * | 9/1972 | Roaf et al. ..................... 606/250 |
| 4,279,248 | A | | 7/1981 | Gabbay |
| 4,670,938 | A | * | 6/1987 | Fowlston ........................ 16/225 |
| 4,802,477 | A | | 2/1989 | Gabbay |
| 5,549,620 | A | | 8/1996 | Bremer |
| 5,620,452 | A | | 4/1997 | Yoon |
| 5,722,976 | A | * | 3/1998 | Brown .......................... 606/281 |
| 5,729,867 | A | * | 3/1998 | Carmichael ..................... 16/225 |
| 5,800,436 | A | | 9/1998 | Lerch |
| 5,928,231 | A | | 7/1999 | Klein et al. |
| 6,007,538 | A | * | 12/1999 | Levin ............................. 606/71 |
| 6,022,351 | A | | 2/2000 | Bremer et al. |
| 6,045,552 | A | | 4/2000 | Zucherman et al. |
| 6,712,821 | B2 | * | 3/2004 | Gabbay .......................... 606/71 |
| 7,361,178 | B2 | | 4/2008 | Hearn et al. |

(Continued)

FOREIGN PATENT DOCUMENTS

DE 196 34 696 4/1998

(Continued)

OTHER PUBLICATIONS

Patent Abstracts of Japan, vol. 2003, No. 06, "Sacrum Fixing Device", Publication No. 2003038504, Publication Date Feb. 12, 2003.

*Primary Examiner* — Thomas C. Barrett
(74) *Attorney, Agent, or Firm* — Lipsitz & McAllister, LLC

(57) ABSTRACT

In a sternum closure device for securing two sternum parts to be connected to one another, comprising an inner contact element to abut the inner face of the sternum, at least one clamping element secured thereto and projecting transversely therefrom, and comprising an outer contact element for abutment on the outer side of the sternum and which can be clamped by means of the clamping element guided through the intermediate space between the sternum parts against the inner contact element, in order to reduce the obstruction by the sternum closure device in the event of a renewed separation of the sternum parts, it is proposed that the inner contact element consists at least partially of a biocompatible plastics material.

6 Claims, 4 Drawing Sheets

U.S. PATENT DOCUMENTS

| | | | |
|---|---|---|---|
| 2005/0065521 A1* | 3/2005 | Steger et al. | 606/69 |
| 2005/0234458 A1* | 10/2005 | Huebner | 606/69 |
| 2005/0278027 A1 | 12/2005 | Hyde, Jr. | |
| 2006/0122611 A1* | 6/2006 | Morales et al. | 606/72 |
| 2007/0038218 A1* | 2/2007 | Grevious | 606/71 |
| 2007/0250059 A1 | 10/2007 | Weisshaupt et al. | |

FOREIGN PATENT DOCUMENTS

| | | |
|---|---|---|
| DE | 299 19 090 | 1/2000 |
| DE | 203 15 612 | 12/2003 |
| DE | 103 26 690 | 1/2005 |
| DE | 10 2004 038 823 | 3/2006 |
| EP | 0 014 823 | 9/1980 |
| JP | 2003-220070 | 8/2003 |
| WO | 02/09602 | 2/2002 |
| WO | 2004/006783 | 1/2004 |
| WO | 2004/016205 | 2/2004 |
| WO | 2004/107998 | 12/2004 |
| WO | WO 2004107998 A1 * | 12/2004 |
| WO | 2006/002744 | 1/2006 |

* cited by examiner

STERNUM CLOSURE DEVICE

This application is a continuation of international application number PCT/EP2007/006846 filed on Aug. 2, 2007.

The present disclosure relates to the subject matter disclosed in international application PCT/EP2007/006846 of Aug. 2, 2007, which is incorporated herein by reference in its entirety and for all purposes.

BACKGROUND OF THE INVENTION

The invention relates to a sternum closure device for securing two sternum parts to be connected to one another, comprising an inner contact element to abut the inner face of the sternum, at least one clamping element secured thereto and projecting transversely therefrom, and comprising an outer contact element for abutment on the outer side of the sternum and which can be clamped by means of the clamping element guided through the intermediate space between the sternum parts against the inner contact element.

A sternum closure device of this type is described, for example, in DE 103 26 690 B4. With the aid of a sternum closure device of this type, the two sternum parts which are separated from one another by a separating cut, can be clamped against one another after an operation and secured relative to one another in such a way that osseous substance is formed in a healing process, which connects the two sternum parts again. The parts of the sternum closure device, which normally consist of a biocompatible metal, in particular of titanium or a titanium alloy, remain in the body.

If a renewed opening of the sternum becomes necessary with the separation thereof into two sternum parts, the parts of the sternum closure device possibly obstruct the separating process, however. This applies, in particular, to the inner contact elements which abut the inner face of the sternum and cannot easily be removed. In the case of the outer contact elements, there is the possibility of lifting these off, but in the case of the inner contact elements there is no possibility of access, however, and it is therefore difficult to sever the sternum with a bone saw.

The object of the invention is to configure a sternum closure device of the above type in such a way that severing the sternum during a renewed operation is facilitated.

SUMMARY OF THE INVENTION

This object is achieved according to the invention in a sternum closure device of the type described at the outset in that the inner contact element consists at least partially of a biocompatible plastics material.

An inner contact element, which consists at least partially of a biocompatible plastics material, can also be severed when severing the sternum, whether with the bone saw or, after the introduction of a bone separating cut, with scissors or a similar instrument. After separation of the inner contact element, the sternum parts can easily be spread apart, so that a body access is created.

Examples of the possible plastics material are polyether ether ketone, polyethylene or polyamide or in particular also resorbable plastics materials, for example polylactide or a polylactide copolymer.

While it is basically possible for the entire inner contact element to consist of plastics material, it is provided according to a particularly preferred embodiment that the inner contact element has a centre part made of plastics material and holding projections connected thereto to secure the inner contact element to the sternum, which consist of metal.

The holding projections, on pressing the inner holding element onto the inner face of the sternum, are pressed into the bone substance and thus secure the inner contact element to the inner face of the sternum. These holding projections should preferably consist of metal as they have to exert large forces. It is therefore advantageous if the inner contact element, on the one hand, has holding projections made of metal, but, on the other hand, has a centre part made of plastics material, which can be severed again in the described manner in the case of a re-operation.

It may, in particular, be provided that the holding projections are arranged in two rows extending on opposing sides of the centre part.

The centre part made of plastics material and the holding projections may be connected in various ways, for example mechanically by screwing etc. However, it is particularly advantageous if the holding projections are embedded in the plastics material. This embedding can take place by injection-moulding around the holding projections with plastics material.

It may be provided, in particular, that the projections are connected to one another by means of a strip-like web, which consists of metal and is connected to the plastics material. A component of this type is preferably configured in one piece.

The web may, in this case, be embedded in the plastics material and the holding projections project from the plastics material.

It is favourable if the web has through openings, through which the plastics material passes, so a close connection is achieved between the web, on the one hand, and the plastics material, on the other hand.

The following description of preferred embodiments of the invention serves for a more detailed explanation in conjunction with the drawings.

DETAILED DESCRIPTION OF THE INVENTION

Figure 1:
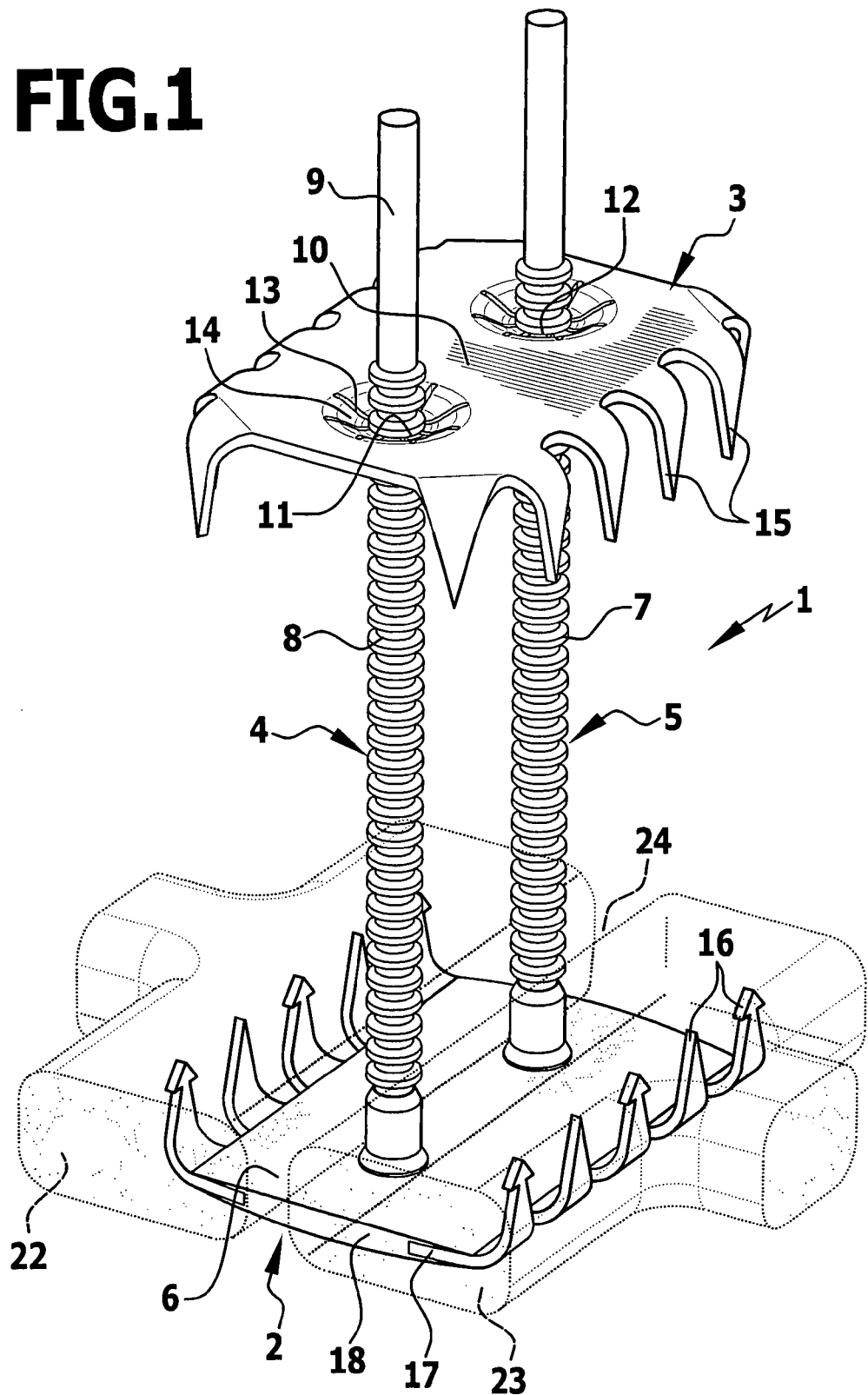
FIG. 1: shows a perspective view of a first preferred embodiment of a sternum closure device comprising an inner contact element with a centre part made of plastics material and holding projections made of metal before the clamping of the contact elements.
Figure 2:
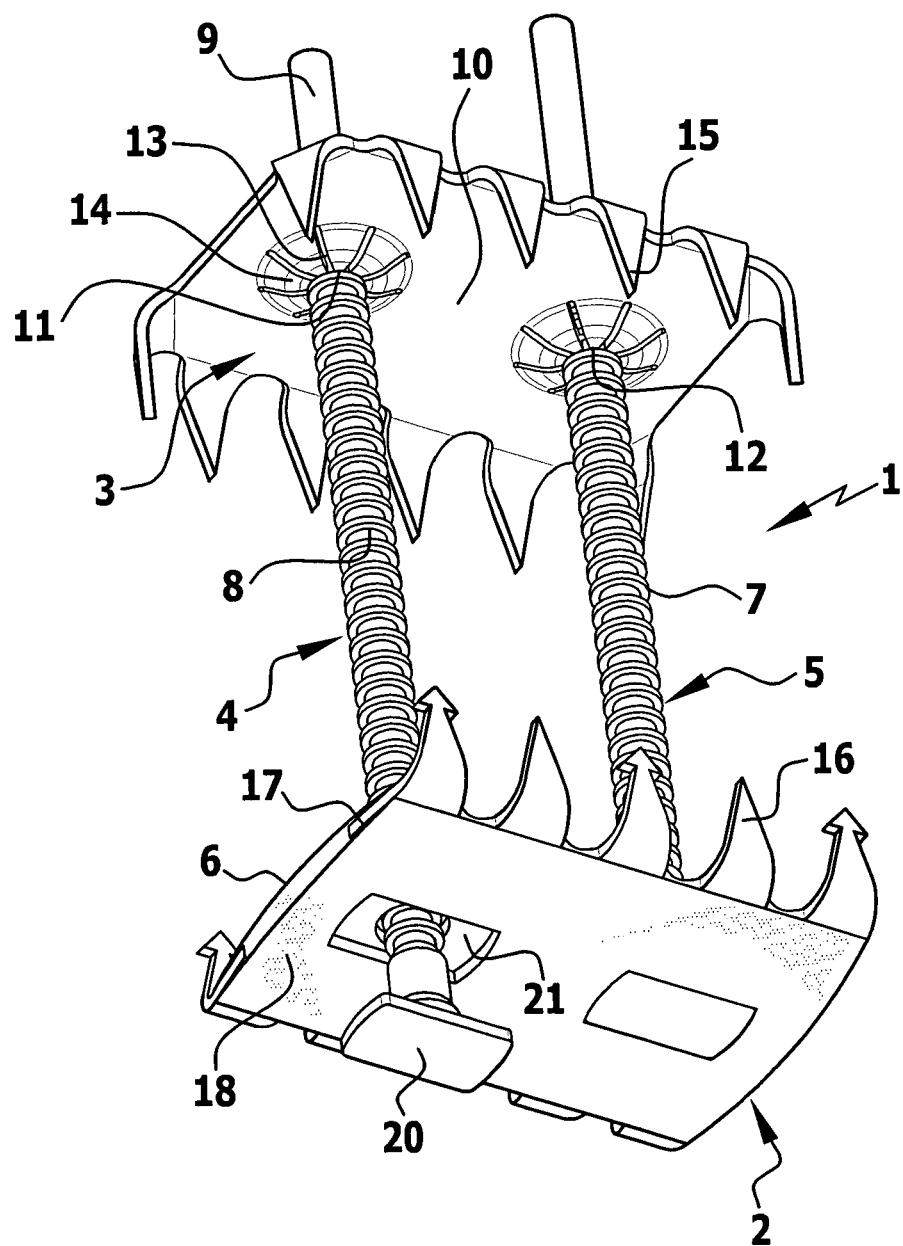
FIG. 2: shows a further perspective view of the sternum closure device of FIG. 1 in a view obliquely from below.
Figure 3:
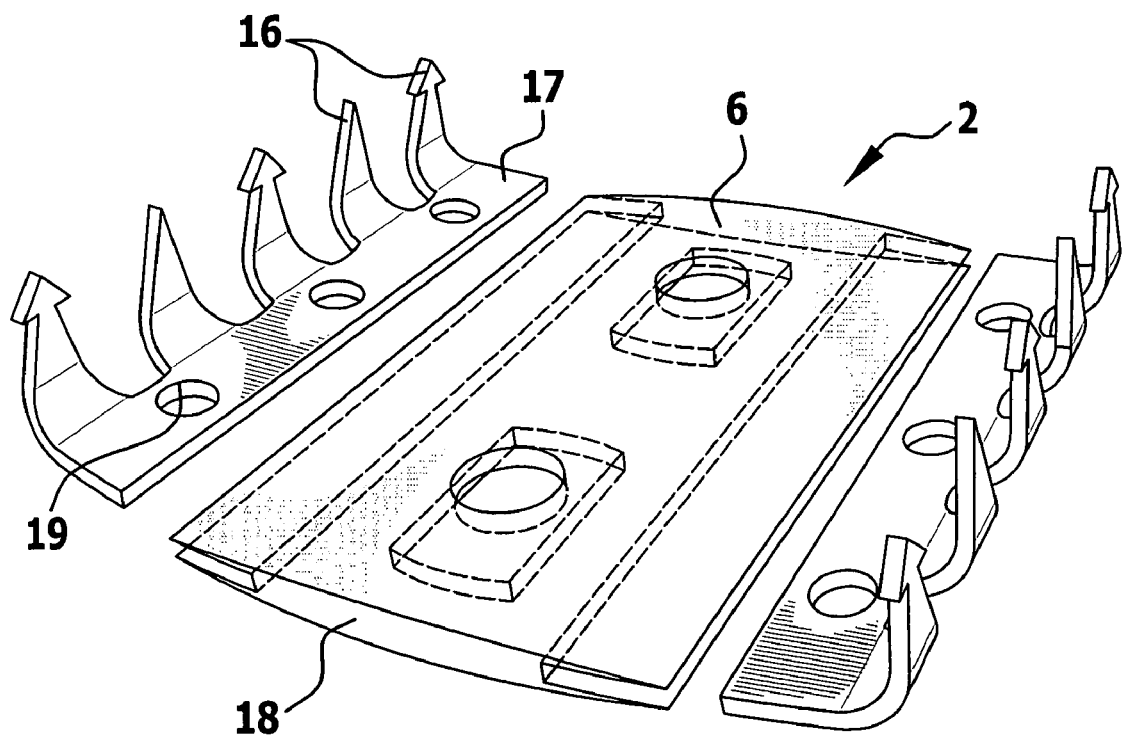
FIG. 3: shows a perspective view of the individual parts of the inner contact element in an exploded view.

The sternum closure device 1 shown in FIGS. 1 to 3 has an inner contact element 2 and an outer contact element 3, which are connected to one another by means of two latching pins 4, 5, acting as a clamping element, and can be clamped relative to one another. The latching pins 4, 5 are held on the plate-shaped inner contact element 2, that is substantially rectangular in the embodiment shown, in such a way that they project perpendicularly from the upper side of the inner contact element 2 and this upper side forms a substantially level contact face 6.

The two latching pins 4, 5, above the inner contact element 2, carry a relatively large number of peripheral ribs 7 and they form therewith a latching portion 8, adjoined toward the free end of the latching pins 4, 5 by a respective extending portion 9 with a smooth outer wall. Placed on the extending portions 9 of the two latching pins 4, 5 is the outer contact element 3, which consists of metal and has an approximately rectangular, plate-like centre piece 10 with a flat lower side, and two apertures 11, 12 which pass through the centre piece 10 and through which the extending portion 9 of the two latching pins 4, 5 projects. Radial incisions 13 emanate from the apertures 11, 12 and divide the edge region of the apertures 11, 12 into tabs 14 which are separate from one another and these may be bent elastically from their starting position if the outer contact element 3 is displaced in the direction of the inner contact element 2 and the tabs 14 slide along the peripheral ribs 7 in the process. As a result, the outer contact element 3 may indeed be displaced in the direction of the inner contact element 2 but not in the reverse direction.

The material of the outer contact element 3 is bent approximately at right angles in the direction of the inner contact element 2 at the two longitudinal edges of the centre piece 10 and forms a row of pointed holding projections 15 there.

The inner contact element 2, on its two longitudinal sides, also carries pointed holding projections 16 pointing in the direction of the outer contact element 3 and these holding projections 16 are in each case connected to one another on one side of the centre piece 10 by means of a web 17, which is configured in one piece with the holding projections 16 and consists of metal, for example of titanium or a titanium alloy. The web 17 in this case runs at a right angle to the direction of the holding projections 16 and lies in the plane of the contact face 6 of the inner contact element 2.

This inner contact element 2, with the exception of the webs 17 and the holding projections 16, is produced from plastics material, either from a biocompatible durable plastics material such as polyether ether ketone, polyethylene or polyamide or of a resorbable plastics material, such as, for example polylactide or a polylactide copolymer. The contact face 6 is part of a plastics material plate 18, which is connected on its two longitudinal edges to the web, for example in that the material of the plastics material plate 18 is injection-moulded around the web. The web 17 is therefore embedded in the plastics material and permanently connected thereto. The connection may be configured to be particularly stable in that openings 19, through which the plastics material passes, are provided in the web 17 (FIG. 3).

The inner contact element 2 thus forms an assembled component, which, apart from the central plastics material plate 18, on the two opposing longitudinal sides in each comprises a web 17 made of metal and provided with holding projections 16. The plastics material plate is reinforced and stabilised by this web, so the holding projections 16 receive the necessary stability which they require when the inner contact element 2 abuts the inner side of a sternum.

The two latching pins 4, 5, at their lower end, carry an enlarged head 20, which engages in a complementary indentation 21 of the plastics material plate and the head and indentation are substantially rectangular so that the latching pin is non-rotatably held on the inner contact element 2. It is basically also possible to surround the head 20 with the plastics material and to embed it completely in order to produce a connection that is as good as possible.

The sternum closure device 1 is applied in a similar manner to a conventional sternum closure device with a metallic inner contact element 2. The application takes place on the inner face of two sternum parts 22 and 23 which are separated from one another by a separating cut and spread apart. The inner contact element 2 is introduced into the thoracic cavity through the intermediate space 24 between the sternum parts, which is widened by the spreading apart of the sternum parts 22, 23 and then, after the two sternum parts 22, 23 have been clamped together, the holding projections 16 of the inner contact element 2 are pressed into the inner face of the sternum parts 22, 23 in that the inner contact element 2 is clamped against the inner side of the sternum parts 22, 23 by pulling on the latching pins 4, 5. By means of a clamping instrument, not shown in the drawing, the outer contact element 3 is then displaced on the latching pins 4, 5 in the direction of the inner contact element 2 until the holding projections 15 from the outer side of the sternum parts 22, 23 have penetrated therein and until the upper side of the inner contact element 2 and the lower side of the outer contact element 3 abut the sternum on both sides and thus durably secure the two sternum parts 22, 23 relative to one another. In this applied state, the projecting parts of the latching pins 4, 5 can be removed.

A plurality of sternum closure devices 1 of this type can thus be applied at a spacing from one another over the length of the intermediate space 24, so that these two sternum parts 22, 23 are secured against one another over the entire length of the separating cut between the two sternum parts 22, 23.

In the event of a renewed separation of the sternum possibly becoming necessary, the outer contact elements 3 are firstly removed. Then a severing of the bone material of the sternum can take place with a bone saw along the latching pins 4, 5. During this severing, either the plastics material of the inner contact element 2 can also be severed or else this plastics material is severed with its own tool, for example with scissors or cutting pliers. As soon as the inner contact element 2 is separated into two parts, the sternum parts 22 and 23 can easily be spread apart, and it is then also possible to lift off the parts of the inner contact element 2 individually from the respective sternum part and to remove them from the rear sternum wall.

In the embodiment of FIGS. 1 to 3, a hybrid mode of construction has been used with an inner contact element 2, which consists of a central centre part made of plastics material and of metallic holding projections.

Figure 4:
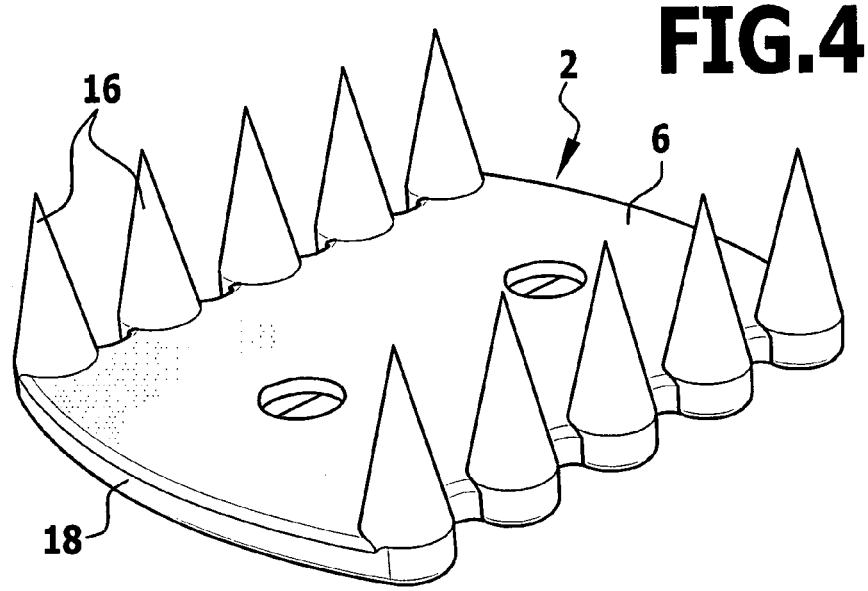
FIG. 4: shows a further embodiment of an inner contact element, which consists completely of plastics material.
Figure 5:
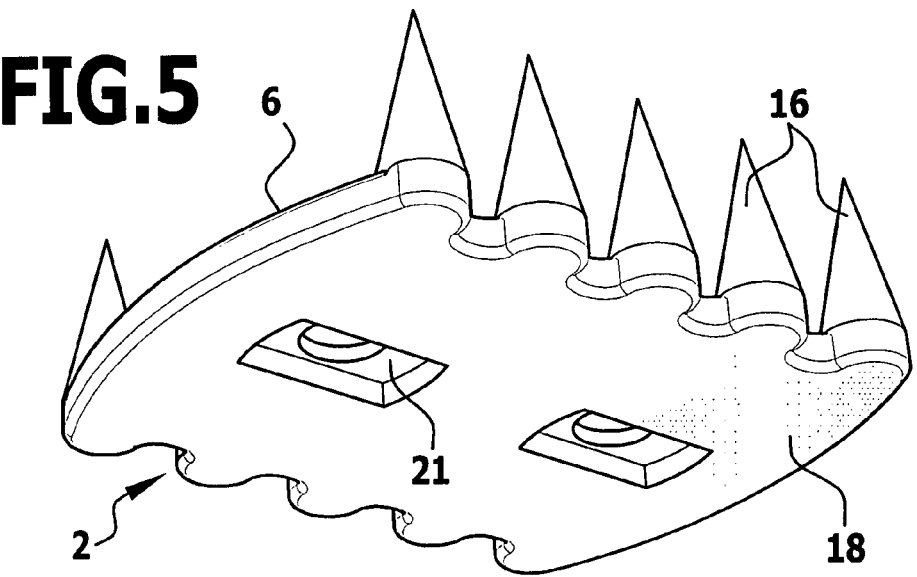
FIG. 5: shows a perspective view of the contact element of FIG. 4 in a view obliquely from below.

In the embodiment of FIGS. 4 and 5, in which mutually corresponding parts have the same reference numerals, a one-piece configuration made of plastics material is selected and in this case the holding projections 16 are thus also manufactured from a plastics material. This inner contact element 2 does not contain any metallic components. It is also easily possible in this configuration, to divide the inner contact element 2 into two parts during a re-operation and to thus make it possible to spread the sternum parts 22 and 23 apart.

The invention claimed is:
1. Sternum closure device for securing two sternum parts to be connected to one another, comprising:
   an inner contact element adapted to abut an inner face of the sternum,
   at least one clamping element secured to and projecting transversely from the inner contact element, and
   an outer contact element adapted for abutment on an outer side of the sternum and which can be clamped by means of the at least one clamping element guided through an intermediate space between the sternum parts against the inner contact element,
   the inner contact element having at least a center longitudinal section running an entire length of the inner contact element consisting of a biocompatible plastics material,
   holding projections connected longitudinal edges of the inner contact element to secure the inner contact element on the sternum, and wherein:
the holding projections are connected to one another by means of strip-like webs, and
the strip-like webs consist of metal and are embedded in and permanently connected to the plastics material at the longitudinal edges of the inner contact element.

2. Sternum closure device according to claim 1, wherein the plastics material is polyether ether ketone.

3. Sternum closure device according to claim 1, wherein the plastics material is a resorbable plastics material.

4. Sternum closure device according to claim 1, wherein the holding projections are arranged in two rows extending on opposing sides of the center part.

5. Sternum closure device according to claim 1, wherein the projections are embedded in the plastics material.

6. Sternum closure device for securing two sternum parts to be connected to one another, comprising:
an inner contact element adapted to abut an inner face of the sternum,
at least one clamping element secured to and projecting transversely from the inner contact element, and
an outer contact element adapted for abutment on an outer side of the sternum and which can be clamped by means of the at least one clamping element guided through an intermediate space between the sternum parts against the inner contact element,
the inner contact element having at least a center longitudinal section running an entire length of the inner contact element consisting of a biocompatible plastics material,
holding projections connected to longitudinal edges of the inner contact element to secure the inner contact element on the sternum, and
wherein:
the holding projections are connected to one another by means of strip-like webs,
the strip-like webs consist of metal and are embedded in the plastics material at the longitudinal edges of the inner contact element, and
the web has through openings, through which the plastics material passes.

* * * * *